United States Patent
Lo et al.

(10) Patent No.: US 9,931,454 B2
(45) Date of Patent: Apr. 3, 2018

(54) DIALYSIS MACHINE HAVING AUTO-CONNECTION SYSTEM WITH ROLLER OCCLUDER

(71) Applicants: Baxter International Inc., Deerfield, IL (US); Baxter Healthcare S.A., Glattpark (Opfikon) (CH)

(72) Inventors: Ying-Cheng Lo, Green Oak, IL (US); Yuanpang Samuel Ding, Libertyville, IL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 196 days.

(21) Appl. No.: 14/702,185

(22) Filed: May 1, 2015

(65) Prior Publication Data

US 2015/0231319 A1 Aug. 20, 2015

Related U.S. Application Data

(63) Continuation of application No. 12/275,982, filed on Nov. 21, 2008, now Pat. No. 9,044,544.

(51) Int. Cl.
*A61M 1/00* (2006.01)
*A61M 37/00* (2006.01)
(Continued)

(52) U.S. Cl.
CPC ............ *A61M 1/28* (2013.01); *A61M 39/20* (2013.01); *A61M 2205/10* (2013.01); *A61M 2205/121* (2013.01); *A61M 2205/7536* (2013.01)

(58) Field of Classification Search
CPC ........ A61M 2205/12; A61M 2205/121; A61M 2205/128; A61M 1/288; A61M 39/18; A61M 39/28; A61M 39/285
(Continued)

(56) References Cited

U.S. PATENT DOCUMENTS

| 1,896,379 A | 2/1933 | Ross |
| 2,145,196 A | 1/1939 | Biggs |

(Continued)

FOREIGN PATENT DOCUMENTS

| EP | 0482858 | 4/1989 |
| EP | 0575970 | 12/1993 |

(Continued)

*Primary Examiner* — Kami A Bosworth
*Assistant Examiner* — William Carpenter
(74) *Attorney, Agent, or Firm* — K&L Gates LLP (57) ABSTRACT

A medical fluid or dialysis system includes an auto-connection mechanism that connects connectors from the supply bags to dialysis cassette ports or cassette supply lines. The system provides for multiple, e.g., four, supply bags, which can be connected to a manifold of the auto-connection mechanism. Tip protecting caps that protect the supply line ends and cassette ports or cassette supply line ends are made to be compatible with the auto-connection mechanism. The auto-connection mechanism removes all the caps and connects the supply lines to the cassette. At least one roller occluder is provided that occludes the supply tubing prior to the tip protecting caps being removed. The roller occludes prevent medical dialysis fluid from spilling out of the supply lines between the time that the caps are removed and connection to the cassette is made.

9 Claims, 10 Drawing Sheets

(51) Int. Cl.
*A61M 1/28* (2006.01)
*A61M 39/20* (2006.01)

(58) Field of Classification Search
USPC .......................................................... 604/151
See application file for complete search history.

(56) References Cited

U.S. PATENT DOCUMENTS

| | | | |
|---|---|---|---|
| 2,249,473 A | 7/1941 | Jackson | |
| 2,721,052 A * | 10/1955 | Hull .................. | F16K 7/063 24/134 R |
| 2,986,160 A * | 5/1961 | Acomb ................... | F16K 7/06 137/505.22 |
| 3,150,639 A * | 9/1964 | Sereda ................... | A01K 7/04 119/73 |
| 3,227,877 A | 1/1966 | Dreyfus | |
| 3,272,398 A * | 9/1966 | Drosman ............... | A47G 19/34 222/210 |
| 3,308,898 A * | 3/1967 | Allen ................... | B65B 39/001 177/113 |
| 3,316,908 A * | 5/1967 | Burke ................... | A61M 5/162 210/448 |
| 3,391,951 A | 7/1968 | Miller | |
| 3,413,097 A | 11/1968 | Jungner | |
| 3,626,938 A | 12/1971 | Versaci | |
| 3,690,779 A * | 9/1972 | Ellis .................... | A46B 11/063 15/144.1 |
| 3,709,222 A | 1/1973 | Devries | |
| 3,738,080 A * | 6/1973 | Reil .................... | B65B 9/13 53/551 |
| 3,780,736 A | 12/1973 | Chen | |
| 3,814,680 A | 6/1974 | Wood | |
| 3,840,011 A | 10/1974 | Wright | |
| 3,847,370 A * | 11/1974 | Engelsher ............ | A61M 1/0078 222/214 |
| 3,916,950 A | 11/1975 | Mongerson et al. | |
| 3,926,556 A | 12/1975 | Boucher | |
| 3,955,922 A | 5/1976 | Moulthrop | |
| 3,957,082 A | 5/1976 | Fuson et al. | |
| 3,986,508 A | 10/1976 | Barrington | |
| 3,994,686 A | 11/1976 | Rauser et al. | |
| 4,056,116 A | 11/1977 | Carter et al. | |
| 4,063,890 A | 12/1977 | Baron | |
| 4,069,153 A | 1/1978 | Gunther | |
| 4,080,965 A | 3/1978 | Phillips | |
| 4,096,859 A | 6/1978 | Agarwal et al. | |
| 4,121,107 A | 10/1978 | Bachmann | |
| 4,141,686 A | 2/1979 | Lewis | |
| 4,169,474 A | 10/1979 | Wagner | |
| 4,173,234 A | 11/1979 | Thomas | |
| 4,196,730 A | 4/1980 | Wilson | |
| 4,201,917 A | 5/1980 | Graentzel | |
| 4,219,055 A | 8/1980 | Wright | |
| 4,219,221 A | 8/1980 | Webb | |
| 4,239,041 A | 12/1980 | Popovich et al. | |
| 4,242,310 A | 12/1980 | Greff et al. | |
| 4,291,701 A | 9/1981 | Bowman | |
| 4,306,976 A | 12/1981 | Bazzato | |
| 4,338,933 A | 7/1982 | Bayard et al. | |
| 4,346,703 A | 8/1982 | Dennehey et al. | |
| 4,387,879 A | 6/1983 | Tauschinski | |
| 4,405,315 A | 9/1983 | Handt | |
| 4,412,834 A | 11/1983 | Kuli et al. | |
| 4,433,244 A | 2/1984 | Hogan | |
| 4,439,193 A | 3/1984 | Larkin | |
| 4,475,900 A * | 10/1984 | Popovich ................ | A61L 2/10 604/28 |
| 4,500,788 A * | 2/1985 | Kulin .................. | A61L 2/10 250/455.11 |
| 4,503,333 A | 3/1985 | Kulin et al. | |
| 4,541,829 A | 9/1985 | Munsch et al. | |
| 4,557,727 A | 12/1985 | Handt | |
| 4,596,551 A | 6/1986 | Golinski et al. | |
| 4,617,012 A | 10/1986 | Vaillcourt | |
| 4,626,245 A | 12/1986 | Weinstein | |
| 4,626,845 A | 12/1986 | Ley | |
| 4,655,753 A * | 4/1987 | Bellotti ................. | A61M 39/18 604/29 |
| 4,655,762 A | 4/1987 | Rogers | |
| 4,675,007 A | 6/1987 | Terry | |
| 4,695,276 A | 9/1987 | Shinno et al. | |
| 4,738,668 A | 4/1988 | Bellotti et al. | |
| 4,755,292 A | 7/1988 | Merriam | |
| 4,769,017 A | 9/1988 | Fath et al. | |
| 4,774,415 A * | 9/1988 | Biegel .................. | A61M 39/18 250/455.11 |
| 4,840,621 A | 6/1989 | Larkin et al. | |
| 4,869,286 A | 9/1989 | Williams et al. | |
| 4,873,446 A | 10/1989 | Kreitmair et al. | |
| 4,878,516 A | 11/1989 | Mathieu | |
| 4,882,496 A | 11/1989 | Bellotti et al. | |
| 4,952,812 A | 8/1990 | Miripol et al. | |
| D310,881 S | 9/1990 | Larkin et al. | |
| 5,014,494 A | 5/1991 | George | |
| 5,047,011 A | 9/1991 | Caron et al. | |
| 5,057,074 A | 10/1991 | Suzuki et al. | |
| 5,125,911 A | 6/1992 | Grabenkort et al. | |
| 5,184,020 A | 2/1993 | Hearst et al. | |
| 5,250,041 A | 10/1993 | Folden et al. | |
| 5,279,605 A | 1/1994 | Karrasch et al. | |
| 5,311,899 A | 5/1994 | Isayama et al. | |
| 5,334,139 A | 8/1994 | Jeppsson et al. | |
| 5,350,357 A | 9/1994 | Kamen et al. | |
| 5,399,156 A | 3/1995 | Lindsay | |
| 5,472,720 A | 12/1995 | Rakhimov et al. | |
| 5,540,265 A | 7/1996 | Polaschegg et al. | |
| 5,542,913 A | 8/1996 | Lindsay | |
| 5,572,992 A | 11/1996 | Kankkunen et al. | |
| 5,583,948 A | 12/1996 | Shibayama | |
| 5,611,506 A | 3/1997 | Berger et al. | |
| 5,612,001 A | 3/1997 | Matschke | |
| 5,647,984 A | 7/1997 | Hovland et al. | |
| 5,707,911 A | 1/1998 | Rakhimov et al. | |
| 5,714,119 A | 2/1998 | Kawagoe et al. | |
| 5,733,457 A | 3/1998 | Hovland et al. | |
| 5,792,419 A | 8/1998 | Williamson et al. | |
| 5,843,379 A | 12/1998 | Kristensen | |
| 5,900,211 A | 5/1999 | Dunn et al. | |
| 5,925,014 A | 7/1999 | Teeple, Jr. | |
| 5,948,247 A | 9/1999 | Gillerfalk et al. | |
| 6,013,918 A | 1/2000 | Bushnell et al. | |
| 6,146,600 A | 11/2000 | Williamson | |
| 6,171,561 B1 | 1/2001 | Williamson et al. | |
| 6,228,332 B1 | 5/2001 | Dunn et al. | |
| 6,234,538 B1 | 5/2001 | Lauer | |
| 6,245,570 B1 | 6/2001 | Grimm et al. | |
| 6,293,921 B1 | 9/2001 | Shinmoto et al. | |
| 6,302,653 B1 * | 10/2001 | Bryant ................... | F04B 51/00 417/383 |
| 6,440,095 B1 | 8/2002 | Utterberg | |
| 6,443,147 B1 | 9/2002 | Matter | |
| 6,461,568 B1 | 10/2002 | Eckhardt | |
| 6,468,424 B1 | 10/2002 | Donig et al. | |
| 6,565,525 B1 | 5/2003 | Burbank et al. | |
| 6,565,803 B1 | 5/2003 | Bolton et al. | |
| 6,696,023 B2 | 2/2004 | Grimm et al. | |
| 6,730,113 B2 | 5/2004 | Eckhardt et al. | |
| 6,736,797 B1 | 5/2004 | Larsen et al. | |
| 6,814,726 B1 | 11/2004 | Lauer | |
| 6,911,025 B2 | 6/2005 | Miyahara | |
| 7,083,605 B2 | 8/2006 | Miyahara | |
| 7,195,615 B2 | 3/2007 | Tan | |
| 7,232,429 B2 | 6/2007 | Moreci | |
| 7,306,197 B2 | 12/2007 | Parrino et al. | |
| 8,836,328 B2 * | 9/2014 | Kruspe ................. | G01N 24/081 324/303 |
| 2004/0025597 A1 * | 2/2004 | Ericson ............ | A61M 5/16804 73/861.52 |
| 2009/0012455 A1 | 1/2009 | Childers et al. | |
| 2011/0125085 A1 * | 5/2011 | McGill ................... | A61M 1/28 604/29 |

(56) References Cited

U.S. PATENT DOCUMENTS

FOREIGN PATENT DOCUMENTS

| WO | 8604674 | 8/1986 |
| WO | 9211046 | 7/1992 |
| WO | 9625214 | 8/1996 |
| WO | 03099355 | 12/2003 |

* cited by examiner

DIALYSIS MACHINE HAVING AUTO-CONNECTION SYSTEM WITH ROLLER OCCLUDER

CROSS-REFERENCE TO RELATED APPLICATIONS

This application claims priority to and the benefit as a continuation of U.S. patent application Ser. No. 12/275,982, filed Nov. 21, 2008, entitled "DIALYSIS MACHINE HAVING AUTO-CONNECTION SYSTEM WITH ROLLER OCCLUDER", the entire contents of each of which are hereby incorporated by reference and relied upon.

BACKGROUND

Automated Peritoneal Dialysis ("APD") is a natural evolution of Continuous Ambulatory Peritoneal Dialysis ("CAPD"), in which the patient introduces the entire contents of a dialysate solution bag into his/her peritoneum and allows the volume to dwell for three to six hours. After the dwell period, the fluid is drained using gravity. The above process is typically repeated three or four times each day as necessary. Working adults may perform an exchange at home before leaving for work, one at work during their lunch hour, one when the patient arrives home from work and one just before the patient goes to bed. Some school-aged patients follow a similar routine except they perform their mid-day exchange at school.

APD machines (sometimes called "cyclers") perform sequential exchanges during the night when the patient is sleeping, making APD a more convenient therapy. Also, the treatment is carried out in the privacy of the patient's home, so that others do not have to know that the patient is on dialysis. It is no surprise that most patients would prefer APD over CAPD.

APD machines require set-up, typically involving the patient making multiple connections between dialysis supply bags and a disposable pumping cassette, which is then loaded into the APD machines. The connections include the removal of caps from the supply lines and the bags and then a physical connection of the lines to the bags. For older patients especially, the connections can be physically challenging. The patient also has to make sure that the lines are connected properly. Besides the supply lines, the disposable cassette can include other lines that do not connect to supply bags, such as a patient line, drain line and heater bag line. The patient has to make sure not to connect one of these lines to the bags.

Recently, auto-connection systems have been developed that connect the cassette and supply bags for the patient, saving the patient from having to perform these labor intensive steps. The auto-connection system has to perform the same steps that the patient had to perform manually, including the removal of caps from the tubes and ports, followed by the physical joining of the supply lines and ports.

When the caps have been removed, and before joining of the tubes and ports, it is possible for dialysis fluid to spill out of the supply lines. This is disadvantages for a number of reasons. First, spilling fluid is wasteful and deprives the patient of the full therapeutic benefit of the bagged solution. Second, liquid spilling into the APD machine can damage the machine. Peritoneal dialysis fluid in particular is sugary and sticky and difficult to clean from between cracks and seams of the machine.

A need accordingly exists for an auto-connection system that prevents fluid from spilling out of the supply tubing after the tubing caps have been removed for connection but before connection has taken place.

SUMMARY

The present disclosure sets forth an auto-connection system that automatically places medical fluid held within solution bags into fluid communication with an apparatus for therapy, such as a disposable pumping and valving cassette. The system is particularly well-suited for a dialysis application, such as peritoneal dialysis ("PD"), which uses bagged dialysis solution or dialysate. The teachings of the present disclosure, however, have application to any type of medical treatment in which connection to one or more solution bag is made.

The auto-connection system, which is part of a dialysis machine in one embodiment, holds a plurality of supply lines. The dialysis machine accepts a disposable pumping cassette having supply ports or supply tubes. The ports or tubes of the cassette are capped as are the supply lines. The auto-connection system moves the supply lines close to the cassette (or supply tubes extending from the cassette). When the supply tubes are adjacent to the cassette, the auto-connection system removes the caps from both the supply lines and the disposable cassette (or cassette supply tubes). As discussed above, at this moment liquid could spill from the supply tubes onto the auto-connection system and/or other components of the dialysis machine.

To prevent the medical fluid spilling, the dialysis machine and auto-connection systems are provided with one or more set of roller occluders. Each roller occluder set can have a single roller or a pair of opposing rollers. In any case, the roller(s) is/are positioned to be able to clamp or occlude the supply tubes prior to the caps being removed from the supply tubes to prevent the above-described dialysate or medical fluid from spilling.

In one embodiment a single pair or set of roller occluder is provided. Each roller rolls on a plurality of roller or ball bearings, so that when the rollers clamp the tubing, the auto-connection mechanism can readily pull the tubing through the rollers. The rollers are pinched together before the supply line cap is removed. The roller occluder can be structured such that a single roller is moved towards a stationary roller, or such that both rollers are moved towards each other to pinch the tubing.

The pinching of the tubing will increase the liquid pressure in the tubing between the rollers and the capped end of the supply line. The auto-connection mechanism, however, pulls the tubing through the roller occluder to increase the length of tubing between the rollers and the capped end of the supply line. The rollers of the occluder prevent liquid from being carried by the translated tubing, resulting in an increase of tubing length without a corresponding increase in liquid volume. This result lowers the pressure in the tubing. If the tubing is pulled far enough through the rollers, a negative pressure is created inside the tubing between the rollers and the capped ends of the tubes, which tends to prevent fluid from spilling out of the tubing when the caps are removed.

Once the caps are removed, the rollers remain pinched. The occluding rollers prevent air from entering the tubing and displacing liquid in the same manner as holding an end of a straw prevents liquid from spilling out of the straw. The fluid accordingly remains in the tubing and does not spill out to the environment. The auto-connection system moves the supply tubing into communication with the disposable cassette (or cassette supply tubes), after which the roller occluder is released from the tubing, allowing supply liquid to be pumped from supply bags or containers to the disposable cassette and from the cassette to the patient, heater or other destination.

In a second embodiment, two pairs of roller occluders are used. One pair is located closer to the supply line ends/caps than is the second pair. The first or inner roller occluder is occluded in the beginning of the auto-connection sequence, while the second or outer roller occluder is released or not occluding.

Like above, the tubing is pulled through the clamped roller occluder towards the cassette (or cassette lines), increasing the volume within the tubing without a corresponding increase in fluid volume between the clamped roller occluder and the capped ends of the supply tubes. The first or inner occluder stays closed, while the second or outer occluder stays open until the supply tubes engage the port or line caps. Then, before the auto-connection mechanism pulls the supply lines and cassette caps off of the cassette or cassette lines, the inner roller occluder opens and the outer roller occluder closes to pinch the tubing. The releasing of the inner roller occluder allows the corresponding pinched tubing to recover or open and to increase further in volume without a corresponding increase in fluid volume. The pinching of the outer roller occluder prevents air from replacing liquid in the open supply line as discussed herein.

It is accordingly an advantage of the present disclosure to provide an improved dialysis system having an automated setup procedure.

It is another advantage of the present disclosure to provide an improved supply line auto-connection feature for medial fluid therapy.

It is a further advantage of the present disclosure to provide an auto-connection system and method that prevents dialysis fluid from spilling out of the supply line tubes.

Additional features and advantages are described herein, and will be apparent from the following Detailed Description and the figures.

DETAILED DESCRIPTION

The description below for FIGS. 1 and 2A to 2G is derived from U.S. patent application Ser. No. 11/773,750 ("the '750 Application"), entitled "Dialysis System Having Supply Container Auto-connection", filed Jul. 5, 2007, assigned to the assignee of the present disclosure, the pertinent portions of which are incorporated herein expressly by reference. To understand the tubing occluders of the present disclosure, it is helpful to first understand the workings of a tubing auto-connection system. Referring now to FIGS. 1 and 2A to 2G, instrument 10 in an embodiment of the '750 Application includes input devices 12 and a display device 14. Input devices 12 can be a separate electromechanical devices as illustrated and/or can include a touch screen overlay operable with display device 14.

Figure 1:
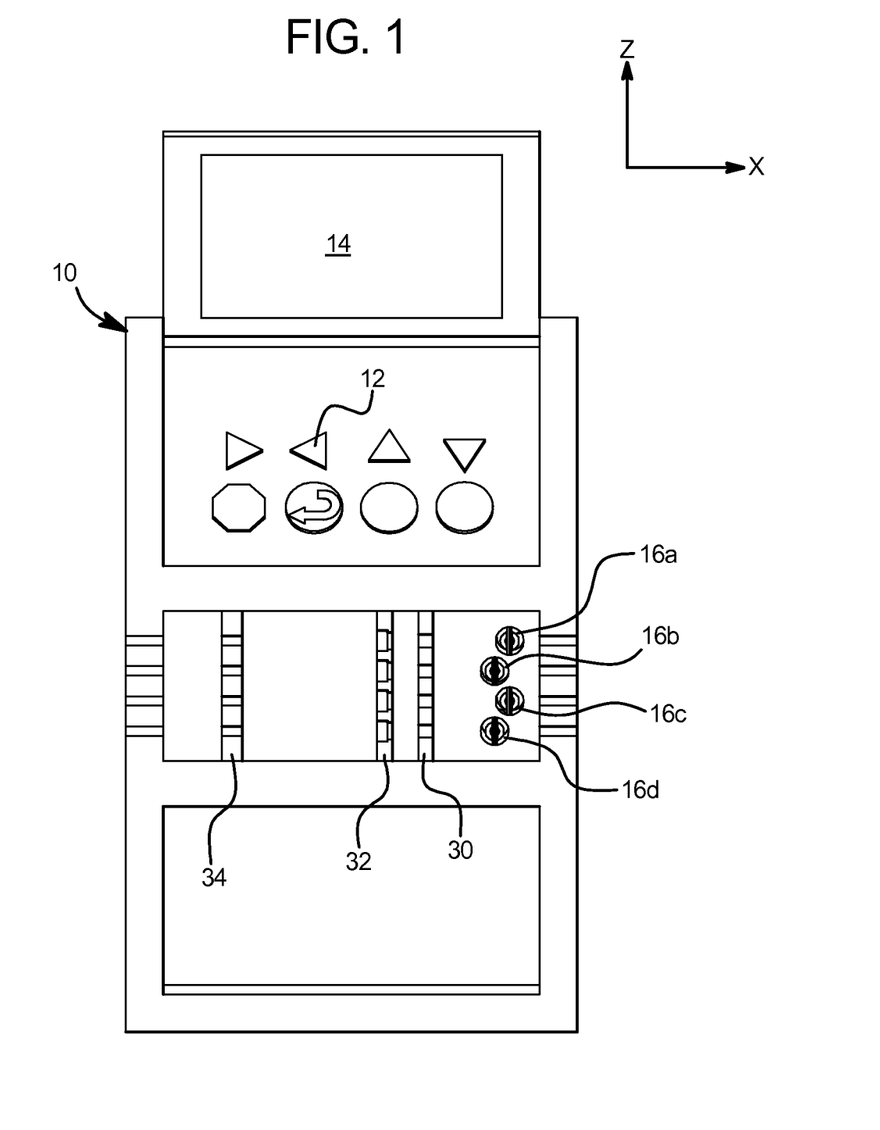
FIG. 1 is an elevation view of a dialysis machine having an auto-connection system that is incorporated herein by reference.

Instrument 10 includes pinch clamps or pinch valves 16a to 16d (referred to collectively herein as pinch valves 16 or generally, individually as pinch valve 16), one valve 16 for each supply bag pigtail or line 18a to 18d (referred to collectively herein as bag supply lines 18 or generally, individually as supply line 18) extending from a respective medical fluid or dialysate supply bag (not illustrated). Pinch valves 16a to 16d are positioned to hold and occlude pigtails 18a to 18d, respectively, when (i) connectors 20 at the end of the pigtails 18 are attached to a stationary connector holder 30 of the auto-connection mechanism of the '750 Application and (ii) the tip protectors 22 protecting each connector 20 are attached (before removal) to a moveable tip protector removal carriage 32 of the auto-connection mechanism of the '750 Application. Tip protector removal carriage 32 is also configured to remove cassette connector 26 tip protectors 28 as shown below.

Pinch valves 16 are opened, e.g., sequentially, to allow fluid to be withdrawn sequentially from supply bags 40. Valves 16 in an embodiment are closed automatically if there is a need to reload cassette 28 after supply bags 40 have been connected. Stationary holder 30 holds supply bag pigtail connectors 20 stationary during the auto-connection process of the '750 Application.

FIG. 1 also illustrates a moveable connection carriage 34, which holds the cassette supply line connectors 26/tip protectors 28 at the end of cassette supply lines or ports 24a to 24d (referred to collectively herein as cassette supply lines 24 or generally, individually as cassette supply line 24), which are connected to a disposable cassette (see cassette 50 below). The individual holders of stationary holder 30 and moveable carriages 32 and 34 are aligned in the Z-direction as shown by the coordinate system in FIG. 1.

Moveable carriage 32 moves in the +X and −X directions to remove tip protectors 22 from connectors 20 and tip protectors 28 from cassette connectors 26. Moveable carriage 32 also moves in the +Y and −Y directions (out of and into the page, respectively) to pull the removed tip protectors 22 and 28 out of the way for supply line to cassette connection and possibly to reload the tip protectors. Moveable carriage 32 in an embodiment uses to an X-Y gantry system, as described in the '750 Application, to perform the multiple direction maneuvers of moveable carriage 32.

Moveable carriage 34 moves in the +X and −X directions to push cassette connectors 26 of cassette supply lines 24 into sealed communication with connectors 20 of supply lines 18. Here, moveable carriage 34 can be threaded and receive a ball screw supported on two ends by bearings and driven by a stepper motor to the carriage back and forth in a precise manner in the +X and −X directions.

Figure 2A:
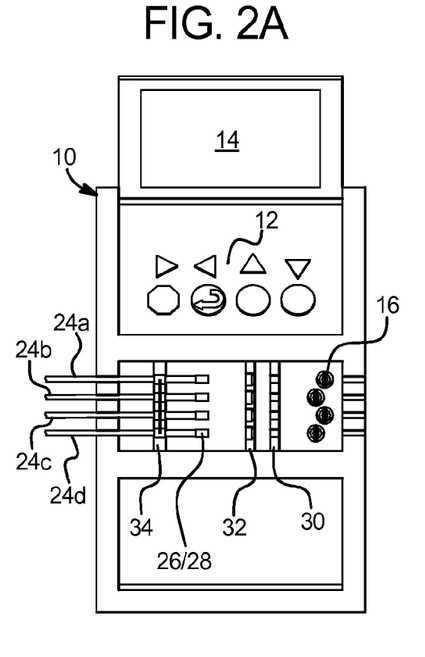
FIGS. 2A to 2G illustrate one auto-connection sequence for the dialysis machine and auto-connection system of FIG. 1, incorporated by reference.

Referring now to FIGS. 2A to 2F, one auto-connection sequence of the '750 Application for the mating of supply bag connectors 20 to the cassette connectors 26 is illustrated. In FIG. 2A, four cassette connectors 26/tip protectors 28 of a cassette supply line set connected to a disposable cassette (not seen) are loaded into the group holder of moveable carriage 34. Alternatively, an integrated cassette with connectors 26/tip protectors 28 is loaded into the group holder of moveable carriage 34. In this step, cassette 50 is also loaded into the instrument (see below).

Figure 2B:
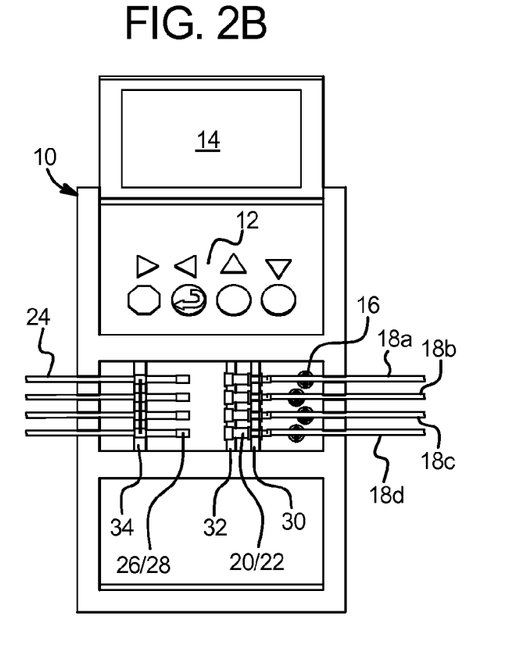

In FIG. 2B, connectors 20/tip protectors 22 located at the end of four supply bag lines 18 are loaded into individual holders of stationary holder 30 and moveable carriage 32. In particular, connectors 20 are loaded into individual holders of stationary holder 30 and tip protectors 22 are loaded moveable carriage 32. In FIG. 2B, tip protectors 22 and 28 are set to be removed automatically from connectors 20 and 26, respectively.

After cassette connectors 26/tip protectors 28 and supply bag connectors 20/tip protectors 22 have been loaded into the auto-connection mechanism of the '750 Application, a cover or door is closed (not illustrated), isolating holder 30, carriages 32 and 34, cassette connectors 26/tip protectors 28 and supply connectors 20/tip protectors 22 from the environment and filtered high-efficiency-particulate-air ("HEPA") or ultra-low-penetration-air ("ULPA") is injected into the sealed compartment as described in the '750 Application.

Figure 2C:
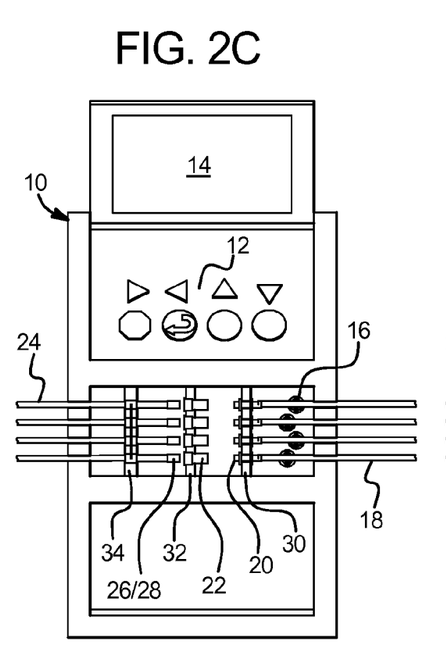

In FIG. 2C, moveable carriage 32 moves in the −X direction (according to coordinate system of FIG. 1) to remove preloaded tip protectors 22 from supply bag connectors 20.

Figure 2D:
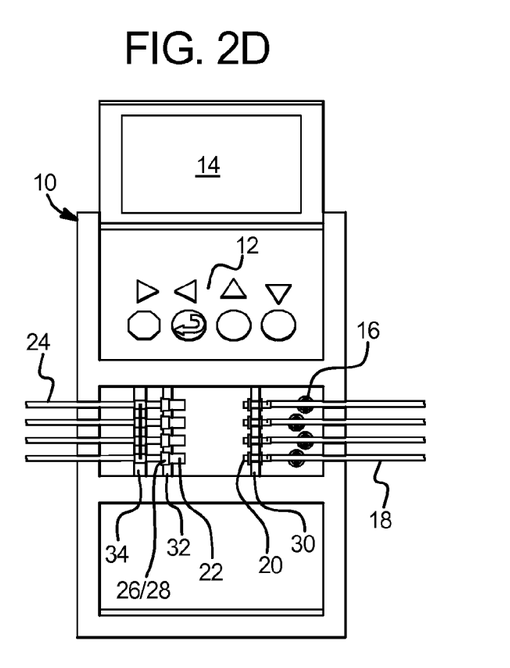

In FIG. 2D, moveable carriage 32 moves further in the −X direction (according to coordinate system of FIG. 1) to lock supply line tip protectors 22 onto cassette tip protectors 28.

Figure 2E:
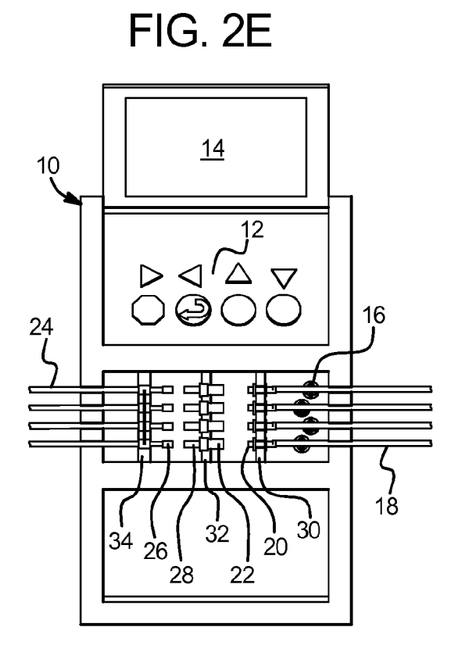

In FIG. 2E, moveable carriage 32 moves in the +X direction (according to coordinate system of FIG. 1) to remove tip protectors 28 from cassette connectors 26.

Figure 2F:
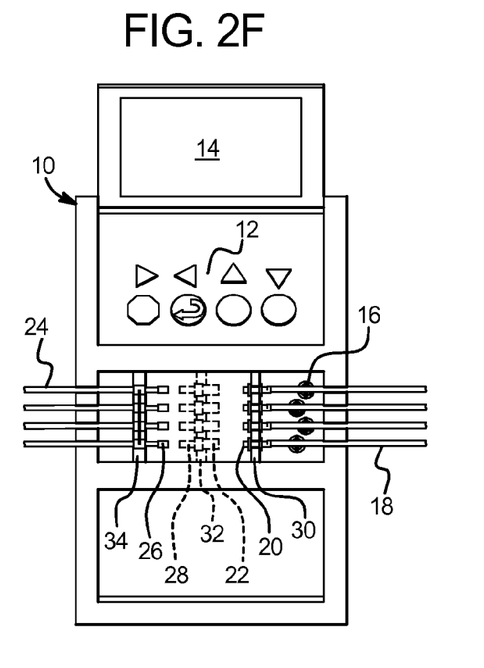

In FIG. 2F, moveable carriage 32 moves in the −Y direction (into page, according to coordinate system of FIG. 1) to move out of the way of supply bag connectors 20 and cassette connectors 26.

Figure 2G:
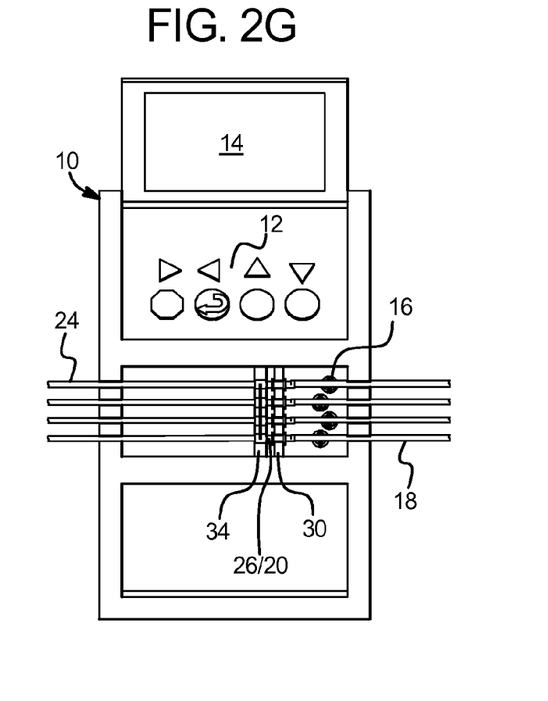

In FIG. 2G, moveable carriage 34 moves in the +X direction (according to coordinate system of FIG. 1) towards stationary holder 30 to push cassette connectors 26 into supply bag connectors 20 and to make sealed supply bag to cassette connections.

Figure 3:
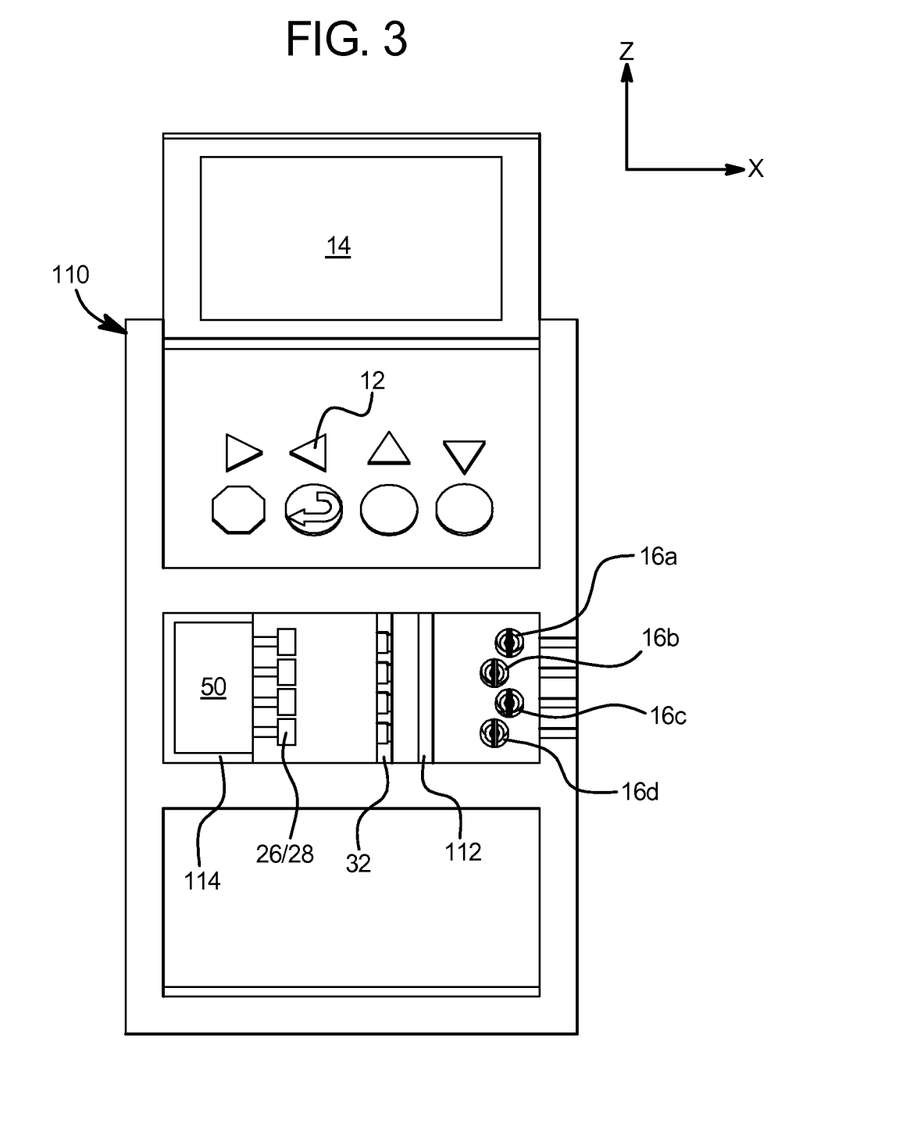
FIG. 3 is a elevation view of one embodiment of a medical fluid machine of the present disclosure, which includes an auto-connection system having a roller occluder that prevents medical fluid spillage when supply line caps are removed.

Referring now to FIG. 3, dialysis instrument 110 of the present disclosure is illustrated. Dialysis instrument 110 includes many of the same components as system 10 of the '750 Application including input devices 12 and a display device 14 that operate with one or more controller, such as a user interface ("UI") controller that in turn is controlled via a supervisory processor/memory. System 110 is computer controlled and can for example include master processing and memory operating with delegate controllers including delegate processing and memory. Master processor and memory can also operate with a safety controller having safety processing and memory. In one embodiment, master processing and memory operates with a delegate motion controller having processing and memory (e.g., programmable or via an application specific integrated circuit ("ASIC")), which outputs to the auto-connection stepper motors and receives inputs, e.g., positional inputs from position sensors. The same or different delegate processor and memory controls solenoid pinch valves 16.

System 110 also includes moveable carriage 32, which moves in the positive and negative X and Y directions, e.g., via a pair of lead screws each driven by a motor, such as a stepper motor. For example, moveable carriage 32 can be threaded and receive a ball screw supported on two ends by bearings and driven by a stepper motor to move carriage 32 back and forth in a precise manner in the +X and −X directions. That X-direction assembly can in turn be threaded, e.g., at a bearing support, and receive a ball screw supported on two ends by bearings and driven by a stepper motor to move the X-direction assembly (including carriage 32) back and forth in a precise manner in the +Y and −Y directions (out of and into the paper, respectively).

Figure 6A:
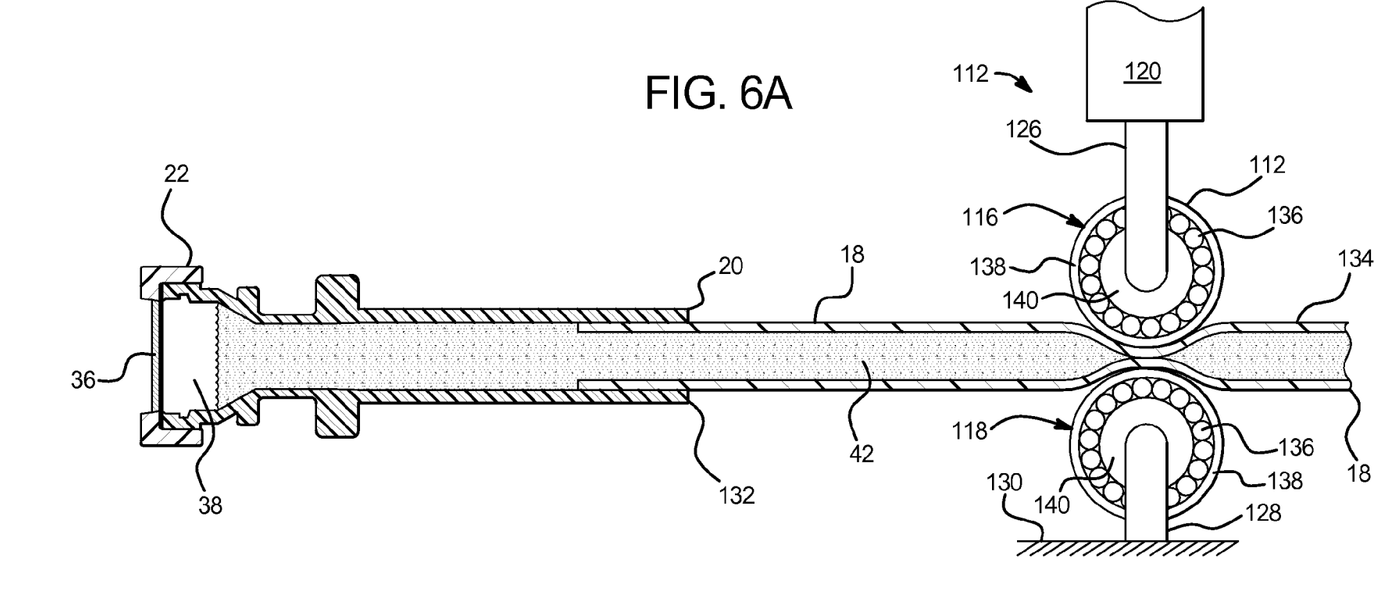
FIG. 6A is an elevation view of one embodiment of a roller occluder of the present disclosure.

System 110 replaces isolating holder 30 of system 10 with a roller occluder 112. Roller occluder 112 can include a pair of rollers (shown in more detail in FIG. 6) that pinch or occlude supply tubes 18 at selective times during the auto-connection sequence to prevent fluid from spilling out of the supply tubes 18. In one embodiment, one of the rollers is solenoid driven in the +Y and −Y directions (out of and into the paper). For purposes of illustration only a single roller of occluder 112 is shown, which is located behind tubes 18 when the supply tubes are loaded. The roller on the outside of the tubes is not illustrated for ease of disclosure. That outside roller is rotatably fixed in one embodiment, e.g., to a door that closes over the disposable set. It is contemplated in an alternative embodiment to make the outer or door roller of occluder 112 an actuated roller, which is actuated instead of or in addition to the inner or machine roller of the occluder.

In another embodiment, the machine roller of occluder 112 is a sole roller and does not operate as a mating pair of rollers. Here, the single roller is translated in the +Y and −Y directions to compress the tubing against a flat surface, such as an inner surface of the door. It should be appreciated, however, that a pair of mating roller occluders, each riding on a set of bearings, reduces the friction applied by the pinching rollers to the tubing 18 when translated through the rollers for reasons discussed herein.

System 110 also replaces moveable connection carriage 34 of system 10 with a cassette mover 114. Here, instead of cassette supply lines 24 running from a cassette that is not seen in FIG. 1, the cassette mover 114 holds the disposable cassette 50 itself. Cassette 50 includes ports 26 protected initially by caps or tip protectors 28. Cassette mover 114 is translatable, e.g., lead screw driven, in the +X and −X directions, similar to moveable connection carriage 34. It should be appreciated that the operation of the roller occluder 112 can be applied to either a machine having moveable connection carriage 34 that carries cassette supply lines 24 or a cassette mover 114 that directly holds and moves cassette 50.

Figure 4A:
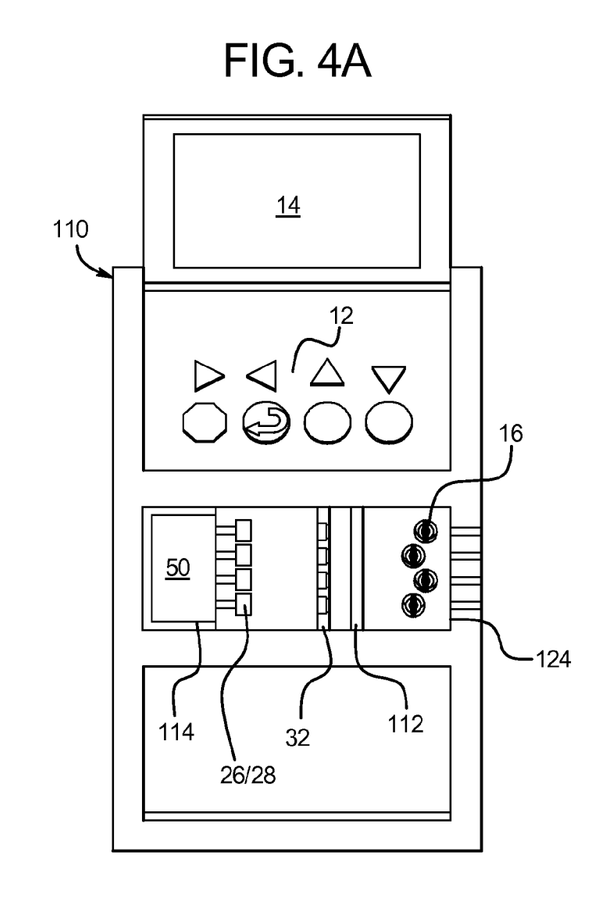
FIGS. 4A to 4G illustrate one auto-connection sequence for the dialysis machine and auto-connection system of FIG. 3.

Referring now to FIGS. 4A to 4F, one auto-connection sequence for instrument 110 that employs an auto-connection mechanism having roller occluder 112 is illustrated. In FIG. 4A, cassette 50 having four cassette ports 26/tip protectors 28 (could have more or less than four) is loaded into cassette mover 114. Alternatively, the arrangement of cassette supply lines 24, cassette connectors 26/tip protectors 28 and moveable carriage 34 is used.

Figure 4B:
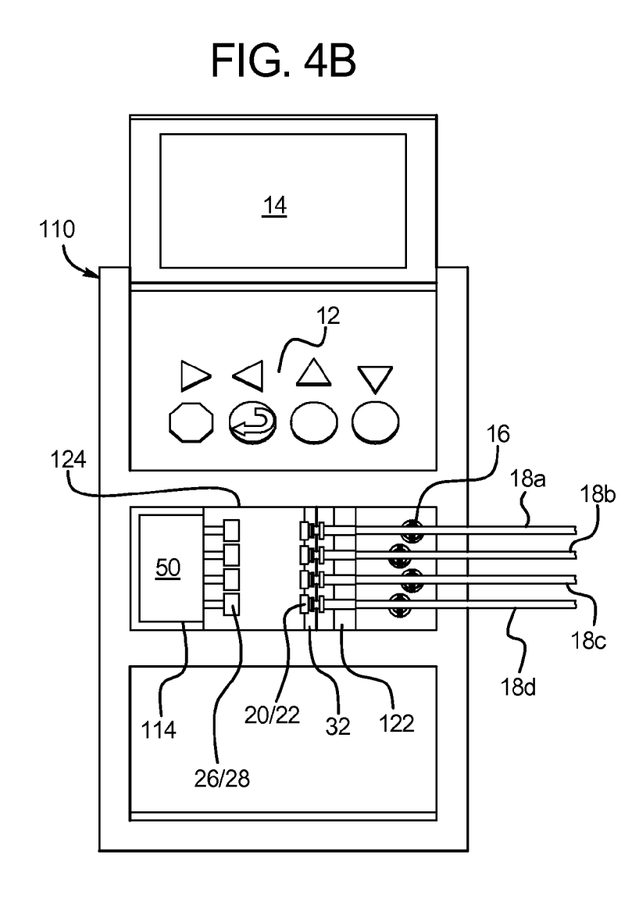

In FIG. 4B, connectors 20/tip protectors 22 located at the end of four supply lines 18 are loaded into individual holders of moveable carriage 32. Here, unlike system 10, moveable carriage 32 supports both connectors 20 and tip protectors 22. Connectors 20 in the illustrated embodiment are banded together as part of an organizer 122. Organizer 122 holds the connectors 20/tip protectors 22 together for easier handling. Organizer 122 slides within auto-connection bay 124, which helps to steady the movement of connectors 20 especially when tip protectors 22 are removed from the connectors 20 and moveable carriage 32 is pulled into the auto-connection bay as shown below in FIG. 4G.

In FIG. 4B, tip protectors 22 and 28 are set to be removed automatically from supply line connectors 20 and cassette ports 26, respectively. In FIG. 4B, the roller occluder 112 is not pinching the supply bag tubes 18 closed, allowing free access to the moveable carriage 32 via the supply lines 18 to load connectors 20/caps 22 into the moveable carriage 32.

After cassette ports 26/tip protectors 28 and supply bag connectors 20/tip protectors 22 have been loaded into the auto-connection mechanism of instrument 110, a cover or door is closed (not illustrated), isolating roller occluder 112, carriage 32 and cassette mover 114, cassette ports 26/tip protectors 28 and supply line connectors 20/tip protectors 22 from the environment. In one embodiment, the closing of the door or cover brings a second roller or occlusion surface into operational position with the roller of occluder 112 illustrated in FIG. 4B. Filtered, high-efficiency-particulate-air ("HEPA") or ultra-low-penetration-air ("ULPA") is injected into the sealed compartment as described in the '750 Application in one embodiment.

Figure 4C:
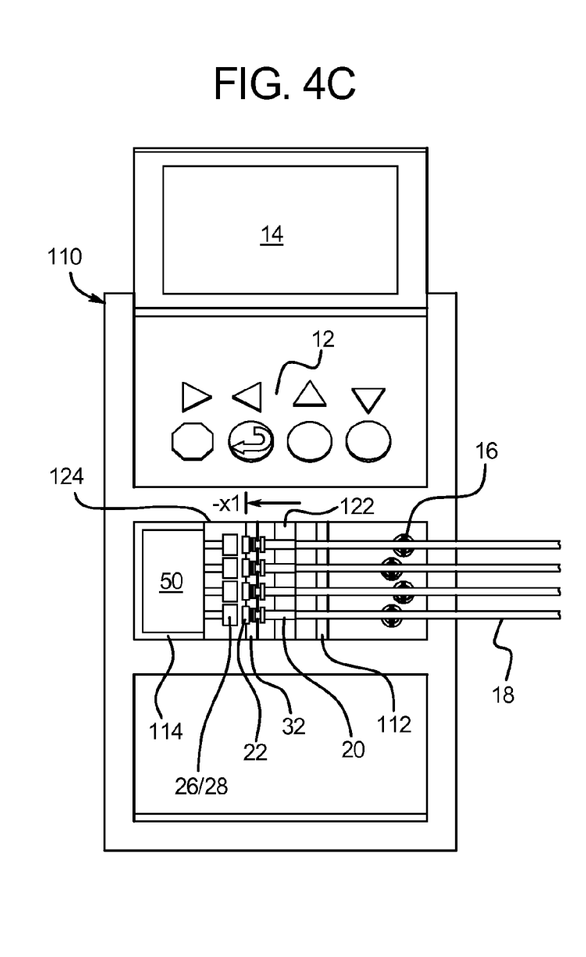

In FIG. 4C, moveable carriage 32 moves in the −X direction for a distance −x1 (according to the coordinate system of FIG. 3) towards cassette 50 and mating ports 26 and tip protectors 28. In FIG. 4C, roller occluder 112 is cause to pinch supply container tubes 18 closed. The clamping of tubes 18 causes pressure in the tubes between the roller occluder 112 and supply line connectors 20/tip protectors 22 to build. However, as the tubes 18 are pulled through roller occluder 112, the occluder prevents supply fluid from moving past the occluder. In this manner, the volume of tubing between occluder 112 and connectors/tip protectors increases, while the volume of fluid in tubing 18, between the roller occluder 112 and connectors 20/tip protectors 22, is fixed, relieving the pressure built from the clamping of the tube and potentially creating a negative pressure in the supply tubes.

Figure 4D:
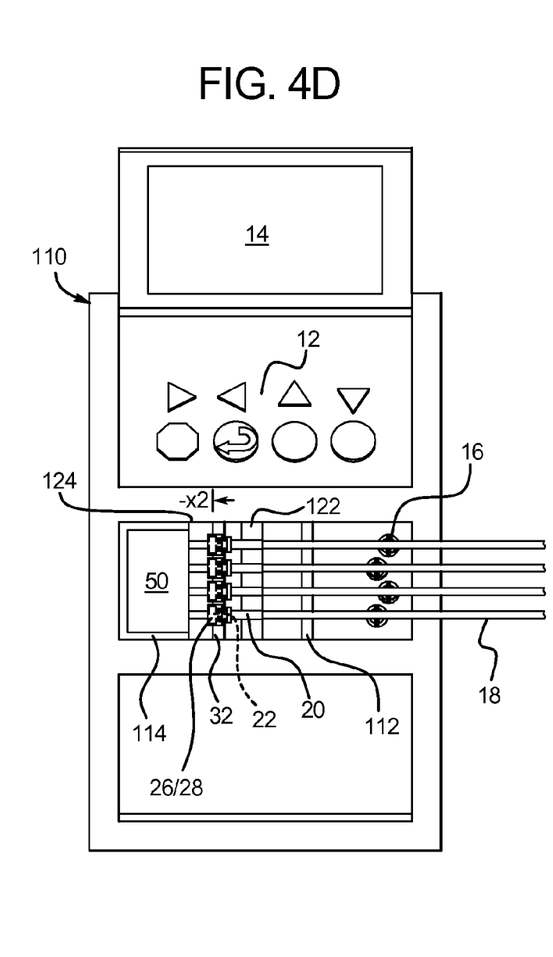

In FIG. 4D, moveable carriage 32 moves further in the −X direction (according to the coordinate system of FIG. 3) for an additional distance of −x2 to lock supply line tip protectors 22 to cassette tip protectors 28. Roller occluder 112 continues to pinch supply container tubes 18 closed. The additional movement further lengthens the tubing 18 between occluder 112 and connectors/tip protectors, while the volume of fluid in tubing 18, between the roller occluder 112 and connectors 20/tip protectors 22, remains fixed, helping to relieve any remaining positive pressure and potentially increasing the negative pressure in the supply tubes.

Figure 4E:
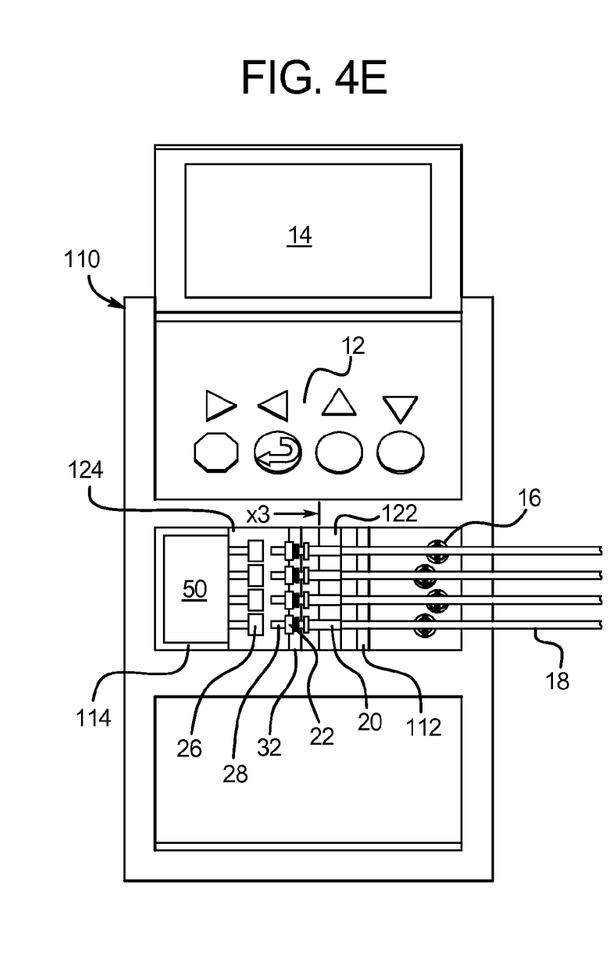

In FIG. 4E, moveable carriage 32 moves in the +X direction (according to the coordinate system of FIG. 3) of a distance of +x3 to remove cassette tip protectors 28 from cassette connectors 26. The +X direction movement pushes some of tubing 18 length through the roller occluder 112 but not enough to build positive pressure in the supply tubes 18 between the roller occluder 112 and connectors 20/tip protectors 22 because travel distance +x3 is considerably less than the combined travel distance of −x1 and −x2 in the opposite direction.

After cassette tip protectors 28 have been removed from cassette connectors 26, pinch valves 16 close to pinch supply tubing 18 into place. Moveable carriage 32 then moves in the −X direction (a distance −x4) to remove supply tube tip protectors 22 from supply tube connectors 20. Because there is no positive pressure in the supply tubes 18, no fluid spills out of the supply tubes 18. The crimped tubing 18, like a straw being held at one end, prevents air from entering the tubing 18 between the roller occluder 112 and the connectors 20, and accordingly prevents the supply fluid, which is now open to atmospheric pressure, from spilling out of supply tubes 18.

Figure 4F:
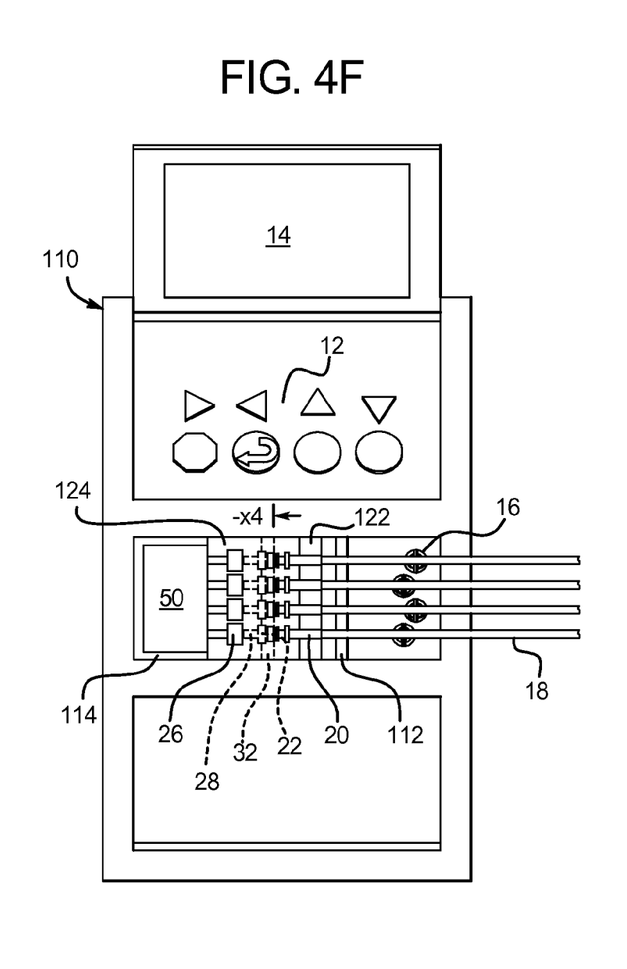

In FIG. 4F, moveable carriage 32 moves in the −Y direction (into page, according to the coordinate system of FIG. 3) to move out of the way of supply bag connectors 20 and cassette connectors 26. Roller occluder 112 remains pinched to prevent the supply fluid, seeing atmospheric pressure at open connectors 20, from spilling out of open-ended tubes 18. As discussed above, organizer 122 holds the connectors 20/tip protectors 22 together for easier handling. When carriage 32 and tip protectors 22/28 are pulled within auto-connection bay 124, organizer 122 continues to slide within auto-connection bay 124 and hold connectors 20 elevationally in place so that ports 26 of cassette 50 can be brought into fluid communication with connectors 20 of supply tubes 18.

Figure 4G:
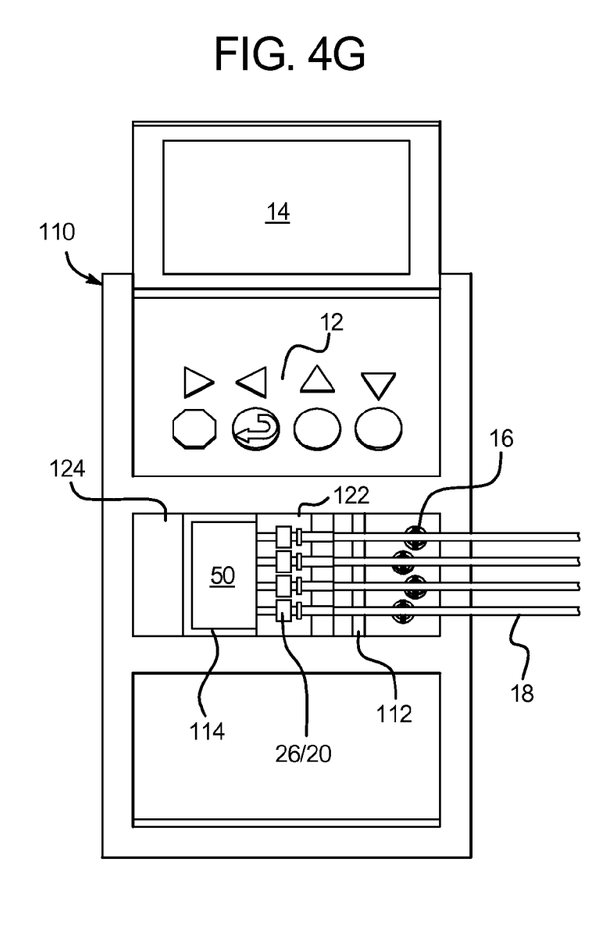

In FIG. 4G, cassette mover 114 moves in the +X direction (according to the coordinate system of FIG. 3) towards organizer 122 to push cassette ports 26 into a connected and fluid-tight relationship with supply bag connectors 20, such that cassette 50 is now sealed to supply lines 18. At this point, roller occluder 112 and pinch valve 16 are released from supply tubes 18, such that machine 110 can actuate pump chambers of cassette 50 to pump supply fluid from one of supply lines 18 to the patient.

In one embodiment, prior to unclamping roller occluder 112 from supply tubes 18, pinch valves 16 are opened and cassette mover 114 translates cassette in the −X direction (according to the coordinate system of FIG. 3) to the cassette 50 position of FIGS. 4A to 4F, which is an operating position at which cassette 50 is pressed against pump actuators for operation. After supply bag connectors 20 are connected to the cassette as shown in FIG. 4G, the pinch valves 16 are then clamped again to close supply lines 18. Roller occluder 112 is then unclamped from supply tubes 18. The desired pinch valve 16 is then opened to allow supply fluid to be pumped from a desired source to cassette 50. This arrangement allows pinch valves 16 to control fluid flow from a desired source, as set forth in the '750 Application.

Figure 5:
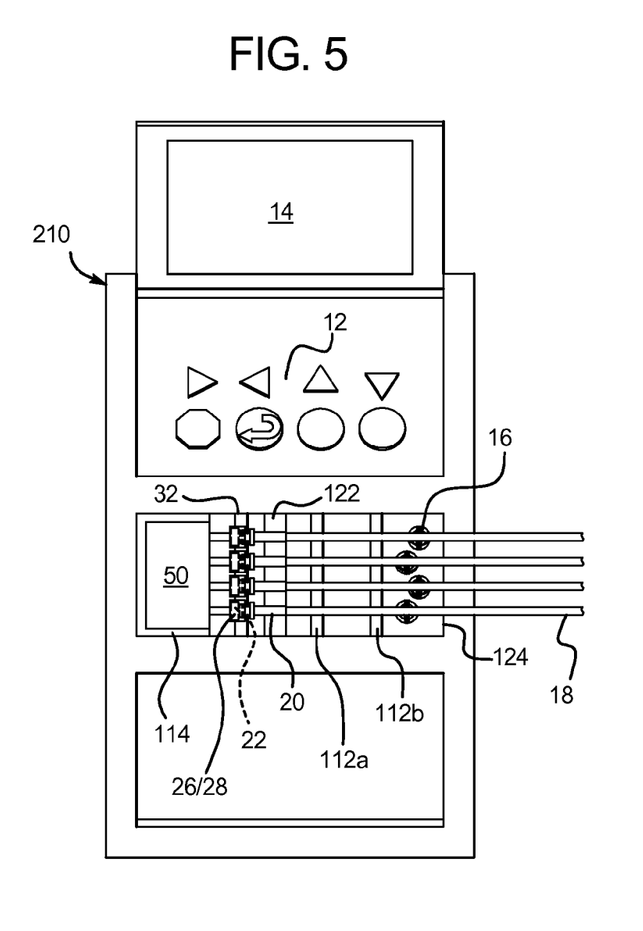
FIG. 5 is a elevation view of another embodiment of the present disclosure including an auto-connection system having a pair of roller occluders that prevent medical fluid spillage when supply line caps are removed.

Referring now to FIG. 5, alternative machine 210 includes a pair of roller occluders 112a and 112b. Second roller occluder 112b can take the form of any of the alternatives for roller occluder 112 discussed above for machine 110.

Machine 210 in FIG. 5 is in the same operational position as machine 110 shown in FIG. 4D above. Prior to the operational position of FIG. 5, both roller occluders 112a and 112b are initially open, allowing free access to the moveable carriage 32 for the supply lines 18 to load connectors 20/caps 22 into the moveable carriage 32 (analogous to FIG. 4B).

When carriage 32 is moved in the −X direction (according to the coordinate system of FIG. 3) to lock supply line tip protectors 22 to cassette tip protectors 28, only inner roller occluder 112a is clamped to pinch supply container tubes 18 closed. Outer roller occluder 112b is not clamped at this time. As with machine 110, the −X direction movement lengthens the tubing 18 between the roller occluder 112a and connectors 20/tip protectors 22, while the volume of fluid in tubing 18, between the roller occluder 112a and connectors 20/tip protectors 22, remains fixed, helping to relieve any remaining positive pressure and potentially increasing the negative pressure in the supply tubes.

When supply line tip protectors 22 and cassette tip protectors 28 have been locked, second roller occluder 112b is also clamped. Both roller occluders 112a and 112b remain clamped while the cassette tip protectors 28 are pulled off of cassette 50. Both sets of roller occluders 112a and 112b remain closed while carriage 32 is moved in the +X direction to pull cassette tip protectors 28 off of cassette ports 26 (analogous to FIG. 4E).

After cassette tip protectors 28 have been removed from cassette ports 26, second roller occluder 112b remains closed but first occluder 112a is opened. The opening of first occluder 112a, between connectors 20 of lines 18 and the crimped occluder 112b, allows the volume of supply lines 18 to further increase without a corresponding increase in supply fluid within those closed sections of supply lines 18.

Next, pinch valves 16 are closed to fix the supply lines 18 in the X direction. Carriage 32 is moved in the −X direction to pull supply lines tip protectors 22 off of supply line connectors 20. Again, because there is no positive pressure in the supply tubes 18, no fluid spills out of the supply tubes 18. The crimped tubing 18, like a straw being held at one end, prevents air from entering the tubing 18 between outer roller occluder 112b and the supply line connectors 20, and accordingly prevents the supply fluid, which is now open to atmospheric pressure, from spilling out of supply tubes 18.

Next, moveable carriage 32 moves in the −Y direction (into page, according to the coordinate system of FIG. 3) to move out of the way of supply bag connectors 20 and cassette connectors 26 (analogous to FIG. 4F). Roller occluder 112b remains pinched to prevent the supply fluid, seeing atmospheric pressure at open connectors 20, from spilling out of open-ended tubes 18. Again, when carriage 32 and tip protectors 22 are pulled within auto-connection bay 124, organizer 122 continues to slide within auto-connection bay 124 and hold connectors 20 elevationally in place so that ports 26 of cassette 50 can be brought into fluid communication with connectors 20 of the supply tubes 18.

Next, cassette mover 114 moves in the +X direction (according to the coordinate system of FIG. 3) towards organizer 122 to push cassette ports 26 into a connected and fluid-tight relationship with supply bag connectors 20, such that cassette 50 is now sealed to supply lines 18 (analogous to FIG. 4G). At this point, roller occluder 112b is released from supply tubes 18, such that machine 110 can actuate pump chambers of cassette 50 to pump supply fluid from one of supply lines 18 to the patient.

In one embodiment, prior to unclamping roller occluder 112b from supply tubes 18, pinch valves 16 are opened and cassette mover 114 translates cassette 50 in the −X direction (according to the coordinate system of FIG. 3) to the cassette 50 position of FIGS. 4A to 4F, which is an operating position at which the cassette is pressed against pump actuators for operation. The pinch valves 16 are then clamped again to close supply lines 18. Roller occluder 112b is then unclamped from supply tubes 18. A desired pinch valve 16 is then unclamped to allow supply fluid to be pumped from a desired source to cassette 50.

Figure 6B:
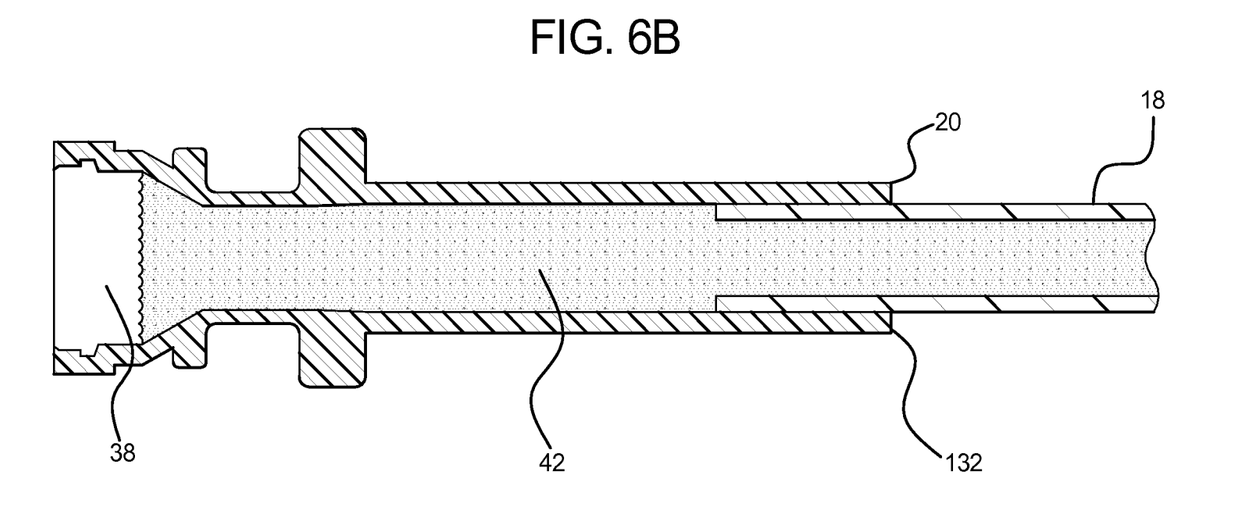
FIG. 6B illustrates the end of the tubing and connector of FIG. 6A with the cap removed.

Referring now to FIGS. 6A and 6B, one embodiment of a roller occluder 112 is illustrated. Roller occluder 112 can be used for either occluder 112a and 112b of machine 210 of FIG. 5. In the illustrated embodiment, roller occluder 112 includes a pair of rollers 116 and 118. Roller 116 is actuated, while roller 118 is fixed rotatably. In an alternative embodiment, only driven roller 116 is provided and fixed roller 118 is replaced by a non-rotating surface. Further alternatively, door roller 118 is actuated, while machine roller 116 is fixed rotatably. Still further alternatively, bother rollers 116 and 118 are actuated.

Roller 116 is actuated by a solenoid 120 in one embodiment, which can be a pneumatically or electrically driven solenoid. For example, solenoid 120 can include a spring that drives plunger 126 outwardly (to pinch supply tubes 18). When a coil of solenoid 120 is energized, a solenoid armature is caused to retract plunder 126 into the housing of solenoid 120 (to open supply tubes 18).

A pneumatically actuated solenoid can be spring actuated to pinch supply tube 18 and placed under a vacuum to open the supply tube. In another embodiment, a pneumatically actuated solenoid is placed under positive pressure to pinch supply tube 18 and placed under a vacuum to open the supply tube.

In the illustrated embodiment, roller 118 is fixed to a portion 130 of the dialysis machine 110/210. Portion 130 can be the door of the machine that closes the outside of the auto-connection bay 124, placing roller 118 into position to be mated with roller 116 of occluder 112. Solenoid 120 is fixed inside of the auto-connection bay 124 of the dialysis machine 110/210.

As seen, when supply tube 18 is pinched, a closed tube section 132 is created between occluder 112 and the distal tip of connector 20. Closed tube section 132 is separated from a supply side section 134 of supply tube 18. Supply tube 18 can be pulled readily through rollers 116 and 118 due to the bearings (e.g., ball or roller bearings) 136 packed between an outer tube 138 and an inner rod 140 of each roller 116 and 118. It may be possible however to eliminate bearings 136 from one or both rollers 116 and 118 as long as the resulting friction does not place undue stress on moveable carriage 32.

Outer tube 138 as shown in FIGS. 4A to 5 extends so as to occlude each supply tube 18 simultaneously. Here, multiple sets of bearings 136 (e.g., one at each end of extended tube 138) can be provided to properly space outer tube 138 relative to inner rod 140. Solenoid 120 is selected so that it can provide enough force to close all supply lines simultaneously.

In an alternative embodiment, outer tube 138 is sized to rotatably occlude only a single supply tube 18. Here, occluder 112 includes a plurality of occluding wheels 116 and 118, operating in tandem as shown in FIG. 6 to occlude a single one of the supply tubes 18. As before, lower occluding wheel 118 could be replaced by a wall or surface depending upon how much friction is desired. Each occluding wheel 116 and 118 can provide a single inner rod 140 about which each tube wheel 138 rotates. Here again, solenoid 120 is selected so that it can provide enough force to close all supply lines (each tube wheel 138) simultaneously. Alternatively, a separate inner rod 140 is provided for each tube wheel 138. Here, each rod 140 can be driven by a separate solenoid 120, potentially eliminating the need for separate pinch valves 16.

Cap 22 of connector 20 in the illustrated embodiment includes or is fitted with a hydrophobia filter 36 that allows air or gas but not liquid or dialysate to pass through the filter. Filter 36 can have the same or substantially the same diameter as the diameter of the opening of connector 20. Also, the illustrated embodiment shows that cap 22 does not include a pieceable membrane. When connector 20 and cap 22 are moved in the −X direction in FIGS. 4C and 4D, the vacuums created by the additional lengths of tubing 18 pulled past occluder 112, without a subsequent volume of fluid being pulled past occluder 112, pull air into tubing 18, forming air pocket 38. When cap 22 is removed from connector 20 via the process specified at FIG. 4F and shown in FIG. 6B, air can enter through the opened end of connector 20 upon movement −x4, however, the air cannot migrate into the fluid to dispel the fluid.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid system comprising:
a medical fluid machine;
a disposable set operable with the medical fluid machine;
a mechanism operable to move at least one medical fluid supply line into connection with the disposable set to allow fluid communication between the at least one medical fluid supply line and the disposable set;
a first occluder positioned to occlude the at least one medical fluid supply line while the at least one medical fluid supply line is being moved into connection with the disposable set;
a second occluder positioned to occlude the at least one medical fluid supply line while the at least one medical fluid supply line is being moved into connection with the disposable set, the second occluder located between the first occluder and the disposable set; and
wherein the first and second occluders and the mechanism are operated such that (i) only the second occluder is occluding the at least one medical fluid supply line at a first time before a cap at an end of the at least one medical fluid supply line is removed; and (ii) only the first occluder is occluding the at least one medical fluid supply line at a second time before the cap is removed.

2. The medical fluid system of claim 1, wherein the first time occurs before the second time.

3. The medical fluid system of claim 1, wherein at least one of the first and second occluders is rotatable to occlude the at least one medical fluid supply line, while the at least one medical fluid supply line is being moved into connection with the disposable set.

4. The medical fluid system of claim 1, wherein the first time occurs while the mechanism is moved to cause the at least one medical supply line to move towards the disposable set to remove at least one cap from the disposable set.

5. The medical fluid system of claim 1, which includes a third time, between the first and second times, in which both the first and the second occluders are occluding the at least one medical fluid supply line.

6. The medical fluid system of claim 5, wherein the third time occurs when the at least one medical fluid supply line is engaged initially with at least one cap of the disposable set to thereafter remove the at least one cap from the disposable set.

7. The medical fluid system of claim 1, which includes a first actuator positioned and arranged to cause the first occluder to occlude the at least one medical fluid supply line, and which includes a second actuator positioned and arranged to cause the second occluder to occlude the at least one medical fluid supply line.

8. The medical fluid system of claim 1, wherein the disposable set includes a rigid part.

9. The medical fluid system of claim 1, which includes a third time after the second time, in which only the second occluder is occluding the at least one medical fluid supply line after the cap of the at least one medical fluid supply line has been removed.

* * * * *